United States Patent [19]
Jen et al.

[11] Patent Number: 5,948,994
[45] Date of Patent: Sep. 7, 1999

[54] MULTI-FUNCTIONAL TEST MACHINE

[76] Inventors: Ming-Hwa R. Jen, Dept. Of Mechanical Engr. Sun-Yat Sen University, 80424 Kaoshiung; Wei-Hwang Lin, Dept. Of Military Engr. Chinese Military Academy, 83000 Feng - Shan, both of Taiwan

[21] Appl. No.: 09/054,081

[22] Filed: Apr. 2, 1998

[51] Int. Cl.⁶ .................................................. G01N 3/02
[52] U.S. Cl. .................. 73/856; 73/857; 73/796
[58] Field of Search .............................. 73/856, 857, 859, 73/860, 796, 853

[56] References Cited

U.S. PATENT DOCUMENTS

| | | | |
|---|---|---|---|
| 4,846,888 | 7/1989 | Gram et al. | 73/856 |
| 4,854,997 | 8/1989 | Shimada | 156/245 |
| 4,869,112 | 9/1989 | Gram et al. | 73/856 |
| 4,928,532 | 5/1990 | O'Connor et al. | 73/856 |
| 5,138,887 | 8/1992 | Pohl | 73/856 |

*Primary Examiner*—Max Noori

[57] ABSTRACT

A multi-functional test machine is provided. The machine includes a frame with a pair of upright columns parallel extended upward from a foundation, an upper crosshead system slidably engaged on the columns and actuated by a pair of hydraulic jacks butting the columns, a ball bearing suspending from a hollow sphere casing in the upper crosshead system to connect with an upper specimen grip and fastened by a plurality of hydraulic buckles, a lower crosshead system fixed to a lower part of the columns including a rotatable hydraulic cylinder and a linear hydraulic cylinder disposed in alignment in the system to rotatably or slidably actuate a actuator shaft to which a lower specimen grip is engaged so that the test machine in capable of self-alignment and carrying out both torsion and tension-compression test for a specimen, this disclosure further includes a series of detective apparatus such as stress sensors, rotatable and linear displacement detectors which send the tension and displacement information of the specimen grips to a computer and automatically make stress compensations to the upper specimen grip.

14 Claims, 6 Drawing Sheets

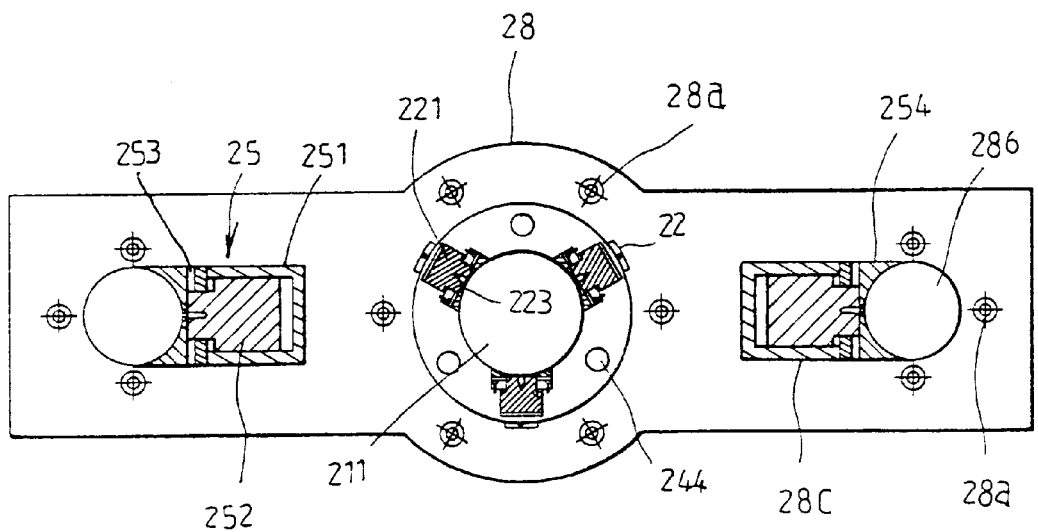
F I G. 2

5,948,994

MULTI-FUNCTIONAL TEST MACHINE

BACKGROUND OF THE INVENTION

The present invention relates to testing machinery, and more particularly to a self-aligning multi-functional test machine which is capable of multi-axle alignment to carry out both torsion and tension-compression tests for a specimen.

Prior art test machine for carrying out tension-compression and swivel test of a specimen includes generally an upper crosshead and a lower crosshead wherein each of the crossheads has an extension and a specimen grip at the end of the extension. The two grips have to align with each other on a center line between the upper and lower crossheads so that the specimen is limited to a linear arrangement to accept a load test U.S. Pat. No. 4,869,112 entitled screw-driven actuator for test from MTS system corporation, which is a device can perform both tension-compression and swivel driven tests. However, the interior of its lower crosshead is composed of a vertical acting oil cylinder and a swivel acting oil cylinder which are rather sophisticated. Besides, there is no any self-aligning system between the upper and lower grips to balance the inclination and shear resulted of the test. Because a linear displacement transducer (LVDT) and a rotation displacement transducer (RVDT) have to be combined therewith, so there is no space inside the lower crosshead to dispose the above self-aligning system. Thus a previously developed self-aligning device by MTS system corporation (U.S. Pat. No. 4,843,888) is adopted to compensate this defect. The self-aligning device includes principally a single pullrod inclination structure which enables to function single axle alignment for a specimen. Nevertheless, it belongs to an externally added equipment that dooms to increase the errors and decrease the distance between the upper and lower crossheads so as to reduce the admittable length of test.

The present invention is arisen to obviate and/or militate the aforediscussed disavantages and provides an upper crosshead including multi-axle alignment system and a lower corsshead including a multiple oil cylinder which is capable of both linear and swivel operations.

SUMMARY OF THE PRESENT INVENTION

The present invention has a main object to provide a multi-functional test machine which is capable of self-alignment and carries out both torsion and tension-compression tests or swivel action of a specimen.

Another object of the present invention is to provide a multi-functional test machine within which the elements are manufactured with conventional process so that they are easy to assemble in order to reduce the cost to manufacture and to win the international competition.

Accordingly, the multi-functional test machine of the present invention comprises an upper crosshead system and a lower crosshead system wherein the upper crosshead system includes generally a spherical seat in corporation with a spherical bearing rod, three prestressed self-shackle hydraulic system and three sensors which adopt induction-feedback method to bring about alignment compensation effect for the upper specimen grip, in order to keep the whole system to be centralized therefore heightening the test accuracy. The lower corsshead system includes a rotatable hydraulic cylinder which enables stable rotation and test of the lower specimen grip, a linear hydraulic cyclinder which is coaxially disposed above the rotatable hydraulic cyclinder and enables linear displacement and test of the lower hydraulic grip, and a three-dimensional displacement hydraulic shaft which connects the lower specimen grip and slides upper and down through the centers of the rotatable and linear displacement hydraulic cylinders so as to enable the grip moving vertically or swiveling alternately. Further, all the above elements are respectively positioned within the upper and lower crossheads so as to increase the distance of the crossheads. It is therefore elongating the specimen of its permissible length.

The present invention will become more fully understood by reference to the following detailed description thereof when read in conjunction with the attached drawings.

BRIEF DESCRIPTION OF THE DRAWINGS

FIG. 2 is a top view with partially sectional view of the upper crosshead of FIG. 1.

DETAILED DESCRIPTION OF THE PREFERRED EMBODIMENT

Figure 1:
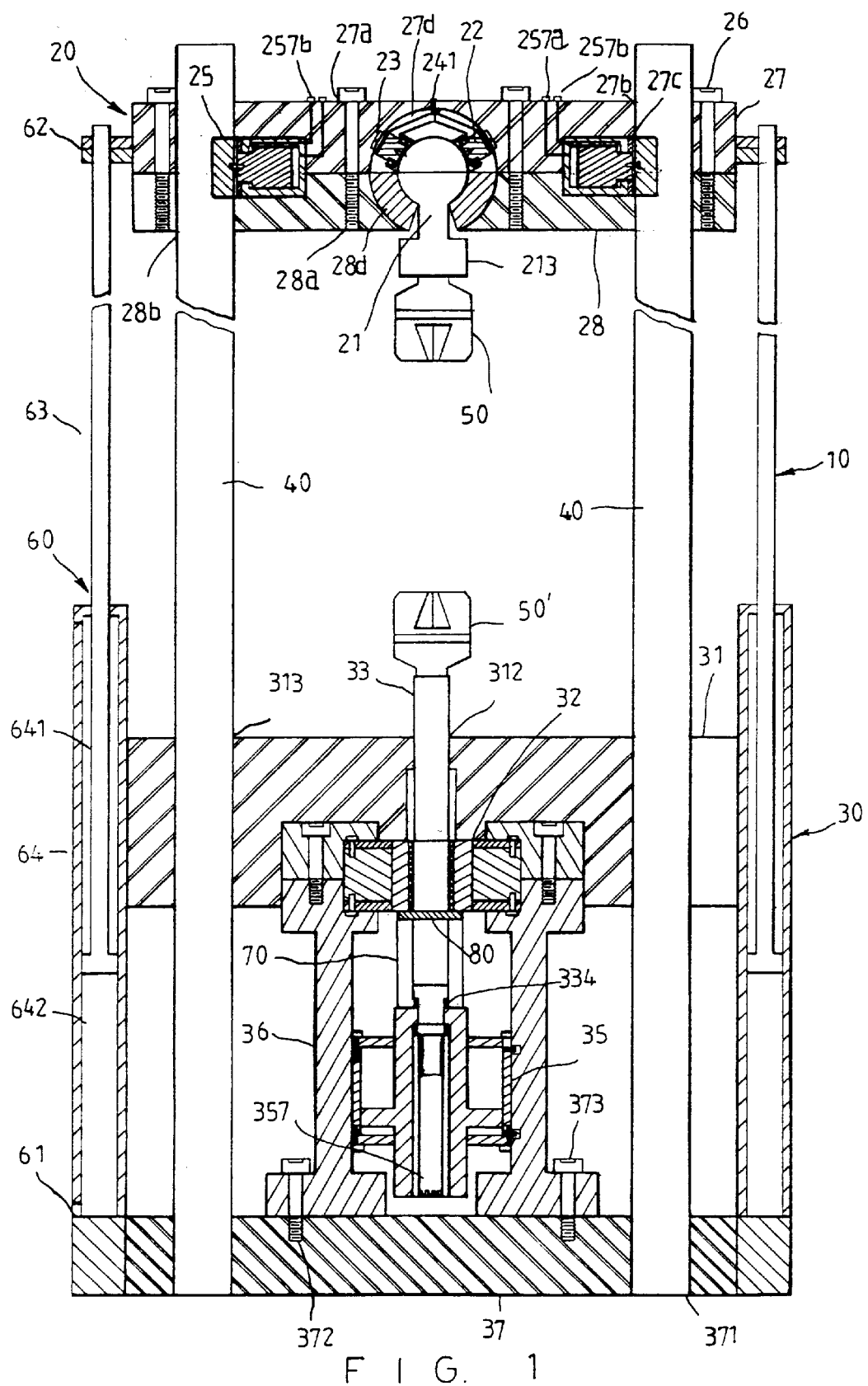
FIG. 1 is an elevational view with partially sectional view of the multi-functional test machine according to the present invention.
Figures 3, 3A, 3B, 3C:
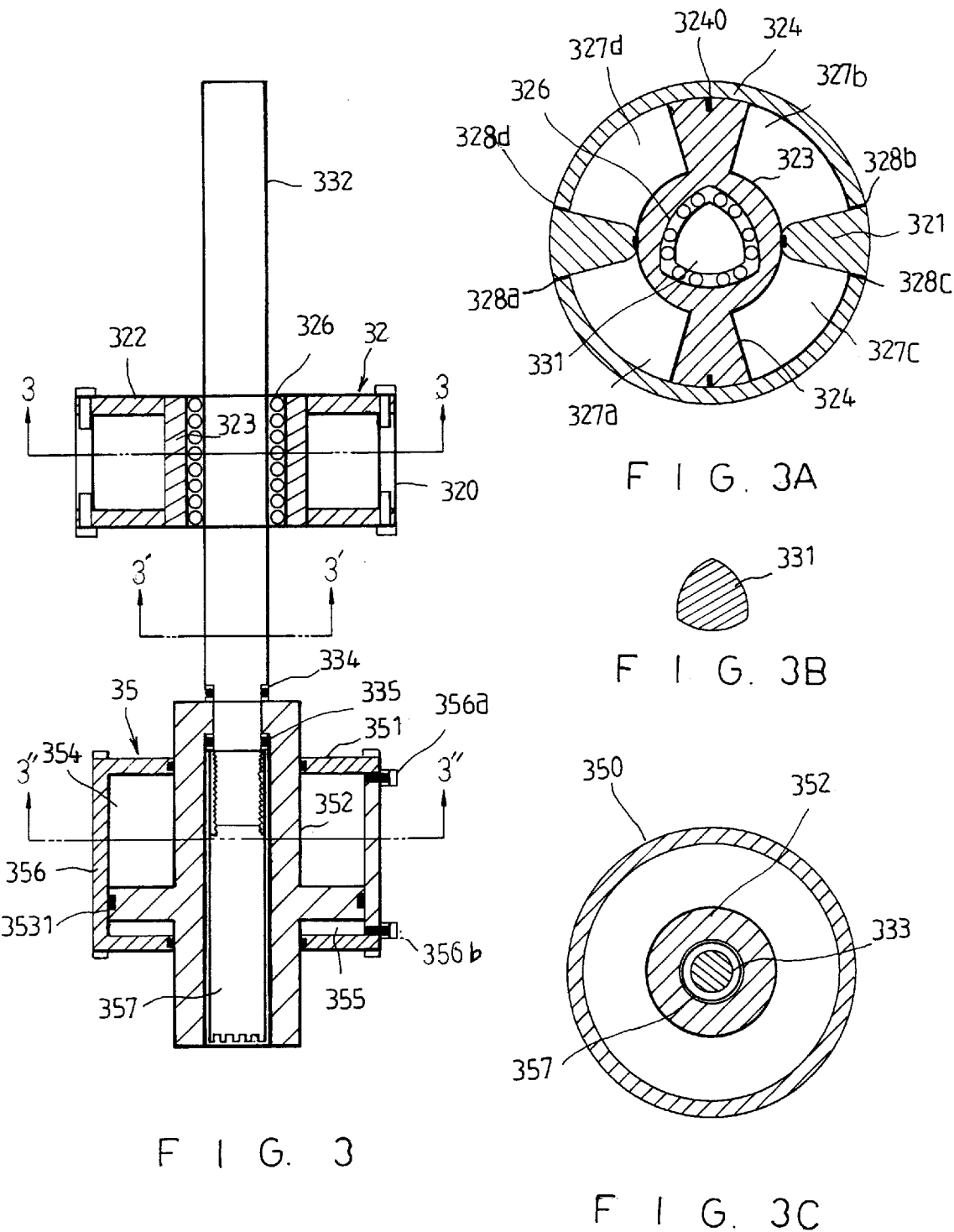
FIG. 3 is an elevational section of the linear hydraulic cylinder and the rotatable hydraulic cylinder of the present invention.
FIG. 3A is a section taken from line A—A of FIG. 3.
FIG. 3B is a section taken from line B—B of FIG. 3.
FIG. 3C is a section taken from line C—C of FIG. 3.

With reference to FIG. 1 and in association with FIGS. 2 and 3, the multi-functional test machine is designated at 10 which comprises generally an upper crosshead system 20 and a lower crosshead system 30, slidably supported by a pair of upright columns 40 and a pair of upper specimen grip 50 and a lower specimen grip 50' respectively secured to the upper and lower crosshead system 20 and 30.

Figure 4:
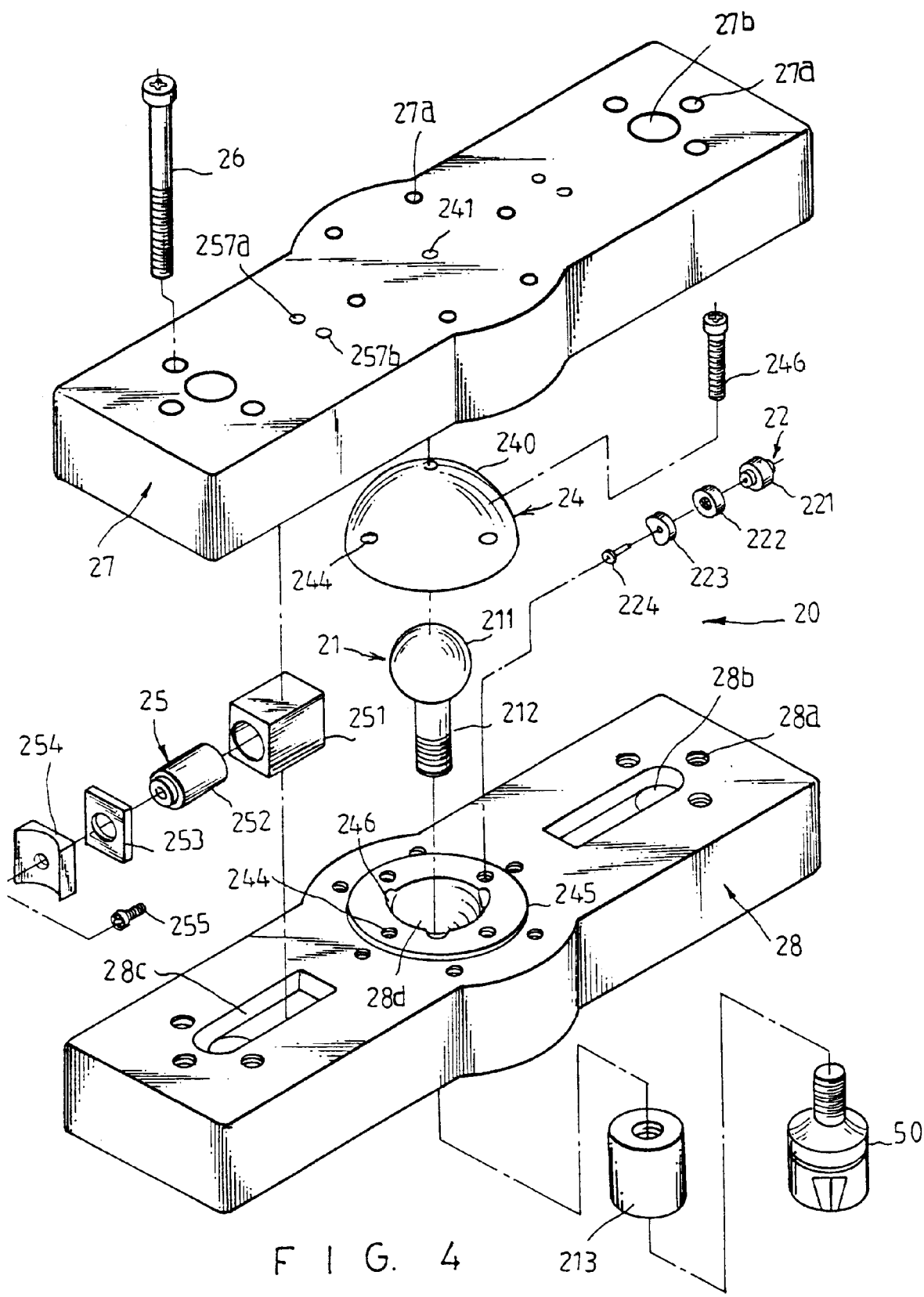
FIG. 4 is an exploded perspective view of the upper crosshead according to the present invention.
Figure 6:
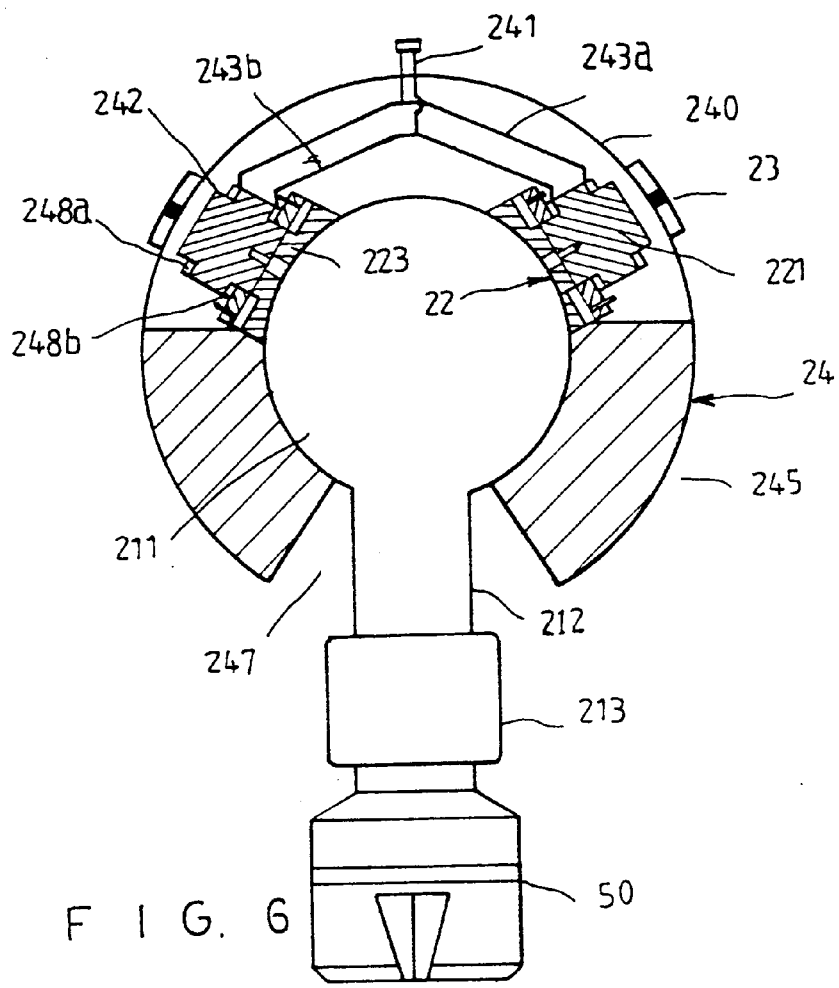
FIG. 6 is an elevational view with partially sectional view indicating the multi-direction hydraulic buckle of the present invention.
Figure 7:
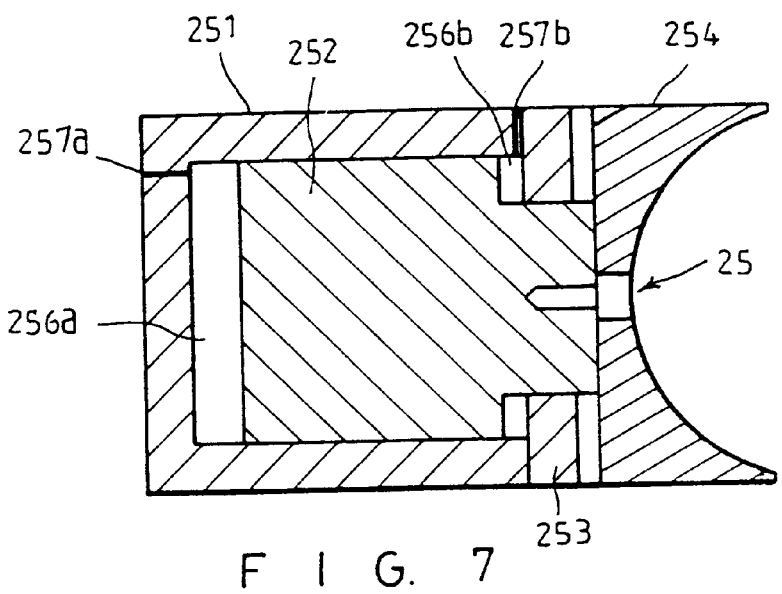
FIG. 7 is a section of the linear hydraulic buckle of the present invention.

The upper corsshead system 20 (as shown in FIGS. 2 and 4) comprises an upper base plate 27 and a lower base plate 28 of rectangular configuration spacedly fastened by the phillips screws 26 through their corresponding screw holes 27a and 28a. Each of the base plate 27 and 28 includes a pair of corresponding circular holes 27b and 28b made in registry with each other in the proximity of their lateral ends for sladably engaging with the upright columns 40, a pair of roughly rectangular corresponding grooves 27c and 28c toward each other so as to form a pair of rectangular chambers therebetween. The upper base plate 27 further includes a hemispherical cavity 27d centrally formed in an under side and the lower base plate 28 further includes a hemispherical central bore 28d made in registry with the hemispherical cavity 27d. A hollow spherical bearing seat 24 which is divided into an upper part 240 and a lower part 245 secured together into the hemispherical central bore 28d by screws 246 through their corresponding vertical screw holes 244. Within the upper part 240, there includes at least three engaging holes 242 respectively connected with a plurality of first conduits 243a and a plurality of second conduits 243b which gather to a convergent port 241 at the top of the upper base plate 27 (as shown in FIG. 6). The lower part 245 includes at least three buckle slots 246 formed spaced apart around the upper rim and made in registry with the engaging holes 242 and tapered central bore 247 made in registry with the hemispherical central bore 28d of the lower base plate 28. A ball bearing rod 21 includes a ball bearing 211 movably engaged into the hollow interior of the sphere seat 24 and a threaded rod 212 extended downward through the tapered central bore 247 and coupled with the upper specimen grip 50 via an internally threaded load cell 213. The specimen grip 50 is of a conventional tapered type including a threaded extension screwed into the load cell 213. At least three hydraulic buckle members 22 respectively and slidably engaged into the engaging holes 242 each includes a first piston 221, an annular ring 222 and a clamp lock 223 which are coaxially and slidably engaged by a pin 224 and wherein the clamp lock 223 has a spherical surface made engageable with the spherical surface of the ball bearing 211. When the hydraulic buckle members 22 engaged into the engaging holes 242, a pair of first and second hydraulic chambers 248a and 248b are respectively defined within each of the holes 242. A stress sensor 23 attaches to the outward end of each of the buckle members 22 for detecting the buckle member of its tensioning condition. A pair of hydraulic brakes 25 slidably disposed into the pair of rectangular chambers between the upper and lower base plate 27 and 28. The brakes 25 (as shown in FIGS. 4 and 7) each includes a hollow rectangular cylinder 251 having a closed end and a cylindrical central opening slidably engageable with a second piston 252 having a threaded screw hole centrally formed within a smaller diameter end, a rectangular cover 253 engageable with the opened end of the cylinder 251 having a circular central hole engageable with the smaller diameter end of the second piston 252 and a second clamp lock 254 having a central hole for fastening itself with the second piston 252 by a screw 255. The clamp lock 254 has a flat surface engageable with the rectangular cover 253 and spherical surface engageable with outer periphery of the upright column 40. When the hydraulic brake disposes into the rectangular chamber, a pair of third and fourth hydraulic chambers 256a and 256b are thus defined therewithin. The chambers 256a and 256b respectively communicate with an outside hydraulic source via a third and fourth conduits 257a and 257b. The arrangement of the hydraulic brakes 25 aims to displaceably positioning the upper crosshead 20 on the upright column 40 and the arrangement of the buckle members 72 facilitate a multi-axle rotation and positioning of the upper specimen grip 50. A pair of hydraulic jacks 60 at outmost lateral sides of the test machine 10 parallel to the upright columns 40 which are designed to actuate the upper crosshead 20 sliding up and down on the column 40 so as to facilitate the upper specimen grip 50 adjusting its vertical positions. The hydraulic jacks each includes a base 61, a fixed end 62 connected to a lateral end of the of the upper crosshead 20, an axial rod 63 of T-shaped section axially inserted into a vertical cylinder 64 to define a fifth and sixth hydraulic chambers 641 and 642 which respectively communicate to an outside hydraulic source (not shown) via a pair of fifth and sixth conduits 601 and 602.

Figure 5:
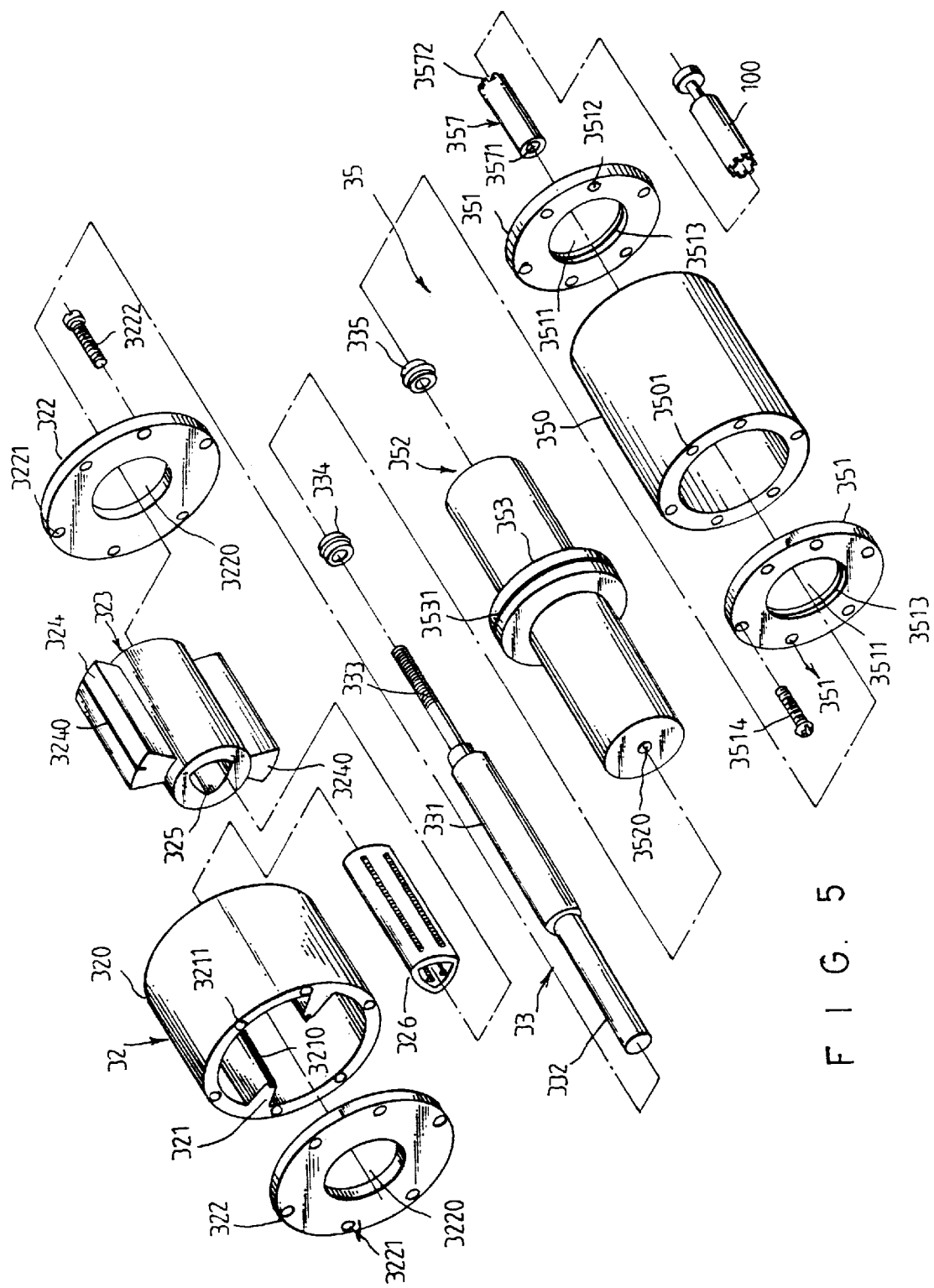
FIG. 5 is an exploded perspetive view showing respectively the linear hydraulic cylinder and the rotatable hydraulic cylinder according to the present invention.

Referring to FIGS. 3 and 5 and FIG. 1 again, the lower crosshead system 30 comprises generally a base seat 31, a rotatable hydraulic cylinder 32 a linear hydraulic cylinder 25, a actuator shaft 33, a linear piston 252, an outer housing 36 and a foundation 37.

The base seat 31 includes a circular concave 311 centrally formed in an under side for receiving the upper part of the housing 36, a central bore 312 communicating with the concave 311 for slidably engaging with the actuator shaft 33 which has an upper end connected to the lower specimen grip 50', a pair of vertical engaging holes 313 adjacent two lateral ends for securing the pair of upright columns 40 therethrough. Further, the lateral ends of the base seat 31 respectively integrate with the verticaly cylinders 64 of the hydraulic jacks 60.

The rotatable hydraulic cylinder 32 includes a tubular casing 320 having a pair of first tapered extensions 321 symmetrically extended inward form an inner periphery with seal 3210 fixed in a groove along the length of the forward end, a pair of upper and lower covers 322 each having a circular hole 3220 in the center, a phirality of screw holes 3221 formed spaced apart adjacent the periphery for respectively fastening themselves to two ends of the tubular casing 321 through their corresponding screw holes 3221 and 3211 by screws 3222, a rotatable piston 323 rotatably disposed into the casing 320 having a pair of second tapered extensions 324 symmetrically extending outward from an outer periphery along the length thereof each including a groove centrally formed along the length for engaging a seal 3240 therein and a central bore 325 of arc lined triangle section for receiving a linear bearing 326 therein. The linear bearing 236 has also an arc lined triangle section engageable into the central bore 325 and a hollow interior slidably engageable with the shaft 32 therein. FIG. 3A shows that the inward ends of the first tapered extensions are closed to the outer periphery of the rotatable piston and the second tapered extensions 324 are closed to the inner periphery of the casing 320 and both with a seal therebetween so that four equal vertical hydraulic chambers 327a, 327b, 327c, 327d are defined within the casing 320. The casing 320 further includes four conduits 328a, 328b, 328c and 328d symmetrically formed spaced apart through hemispheral walls abutting the lateral side of the first tapered extensions 3210 and communicated with external hydraulic sources (not shown). It is understood that if the hydraulic fluid enters into the chambers 327a and 327b via conduit 328a and 328b. The oil existing in the chambers 327c and 327d will be pressed to flow out via conduits 328c and 328d so as to actuate the rotatable piston 323 to rotate clockwise, contrarily, if the hydraulic fluid enters via conduits 328c and 328d, the rotatable piston 323 will be forced to rotate counterclockwise. The alternate rotation of the rotatable piston 323 enables the test machine 10 providing a torsion test function for a specimen. The actuator shaft 33 includes a large diameter portion 331 of arc lined triangular section (as shown in FIG. 3B) slidable engageable into the linear bearing 326, a smaller diameter upper end 332 connected with the lower specimen grip 50' and a threaded lower end 333 axially connected to the upper end a linear piston 352 with a bearing means 334 engaged therebetween.The arrangement of the arc lined triangular section for the actuator shaft 33 and the linear bearing 326 aims to prevent the shaft 33 from rotation but it can be rotated in cencern with the rotatable piston 323. Further, the rotatable cylinder 32 is firmly retained within an upper part of the outer housing 36 and secured by screws 361 (as shown in FIG. 1).

The linear hydraulic cylinder 35 is secured to a lower part of the outer housing 36 and includes a tubular body 350, a pair of upper and lower covers 351 each having a circular central hole 3511 and a plurality of screw holes 3512 formed spaced apart adjacent outer periphery for fastening themselves respectively to two ends of the tubular body 350 through the corresponding screw holes 3501 by screws 3513. The linear piston 352 slidably disposes into the tubular body 350 and includes a cylindrical body of a length longer than the tubular body 350 and a diameter equal to the circular central hole 3511 of the covers 351 so that the piston 352 enables to stretch out of the tubular body 350, a central bore 3521 extended along the length of its cylindrical body so as to permit the insertion of the threaded lower end of the actuator shaft 33 and a fixture 375 from opposite end thereof and an annular flange 353 extended outward from a middle outer periphery having a seal ring 3531 secured into a groove centrally extending around the outer periphery of the flange 353. The flange 353 has an outer diameter equal to the inner diameter of the tubular body 350 so that when the linear piston 352 disposes into the tubular body 350, a pair of upper and lower hydraulic chambers 354 and 355 are defined within the tubular body 350. A pair of conduits 356a and 356b dispose spaced apart through a peripheral wall of the tubular body for communicating the chambers 354 and 355 with an external hydraulics source (not shown). A tubular fixture 357 inserts into the lower end of the linear piston 352 and fasten the threaded lower end of the actuator shaft 33 with a bearing 335 engaged therebetween. The fixture 357 has an internally threaded upper end 3571 made in registry with the threaded lower end 333 of the actuator shaft and a toothed lower end 3572 which is prepared in cooperation with a toothed end of a specific screw driver 100 which has a slotted outer end and by which the fixture 357 enables to tightly engage with the threaded lower end 333 of the actuator shaft 33. FIG. 3c indicates a concentrical relationship between the tubular body 350, the linear piston 352, the tubular fixture 357 and the lower end 333 of the actuator shaft 33. The upper and lower covers 351 of the linear hydraulic cylinder 35 further have a seal ring 3513 secured to the inward circumference of their circular central holes 3511 (as shown in FIGS. 3 and 5) to prevent the oil from leaking out of the tubular body 350. Accordingly, if the hydraulic fluid enters into the upper hydraulic chamber 354 via conduit 356a, the oil existed inside the lower hydraulic chamber 355 will be pressed to flow out via conduit 356b so that the linear piston 352 is forced to move downward relative to the tubular body 350 so as the actuator shaft 33 together with the lower specimen grip 50' that are actuated to slide downward either. Contrarily, if the hydraulic fluid enters into the lower hydraulic chamber 355, both the linear piston 352 and the actuator shaft 33 are forced to shift upward. It is clear that the arrangement of the elements inside the lower crosshead system 30 enables the lower specimen grip to rotate alternately and to shift vertically. Inside the outer housing 36 and between the rotatable hydraulic cylinder 32 and the linear hydraulic cylinder, further includes a rotation displacement detector (RVDT) 80 attached to the lower end of the rotatable hydraulic cylinder 32 and a linear displacement detector (LVDT) 70 connected between the rotatable hydraulic cylinder 32 and the linear hydraulic cylinder 35 which can precisely indicate the vectors of both the linear and rotation displacements inside the cylinders 32 and 35.

The foundation 37 is disposed at a lowermost position of the test machine and juxtaposed with the bases 61 of the hydraulic jacks 60 and includes a pair of circular holes 371 vertically formed spaced apart in proximity of the lateral ends for fixedly securing the lower ends of the upright columns 40 and a pair of the threaded screw holes 372 vertically formed spaced apart in a central upper surface for securing the outer housing 36 by screws 373 (as shown in FIG. 1).

Based on aforediscussed structure, all the movable elements of the present invention are stably arranged that ensures a precise operation.

Referring to FIGS. 1, 3, 6 and 7, in operation, supposedly a non-linear specimen is going to test, first, fix the lower end of the specimen into the lower specimen grip 50' and adjust the height of the upper crosshead system 20 by operating the pair of hydraulic jakes 60 up and down in the manner as described the above until that the upper specimen grip 50 can reach the specimen and grip it, then apply the hydraulic fluid into the chamber 256a of the two hydraulic brakes 25 simultaneously to force the clamp locks 254 moving forward to firmly clamp the upright columns in order to fix the upper crosshead system 20 from any movement, and then apply hydraulic fluid into the chambers 248a of the three hydraulic buckle members 22 simultaneously to fix the ball bearing 21 from rotation after it gets aligned with the specimen and the lower specimen grip 50' so that the test can begin. If carrying out a torsion or rotation test, operate the rotatable hydraulic cylinder 32 by applying hydraulic fluid into chambers 327a and 327b via conduits 328a and 328b to force the piston 323 rotating clockwise or contrarily, applying the hydraulic fluid into chambers 327c and 327d via conduits 328c and 328d to force the piston 323 rotating counterclockwise. Meanwhile the rotation displacement detector (RVDT) 80 simultaemously send the vector of rotation displacement to an external computer (not shown) in which the torsion test result is readable.

If carry out a tension-compression test, operate the linear hydraulic cylinder 35 by applying the hydraulic fluid into chamber 354 or 355 via conduit 356a or 356b so that the linear piston 352 is forced to move up or down to actuate the lower specimen grip 50' moving vertically to carry out the tension-compression test and the linear displacement detector (LVDT) 70 simultaneously send the result of the displacement vector to an external computer, too.

During the above tests, the stress sensors 23 of the hydraulic buckle members 22 will automatically send the information to an external computer and simultaneously release buckle members if any of the three hydraulic buckle members 22 is stressed unevenly scattered. When the stress state is equivalently even the hydraulic buckle members 22 will clamp and fix the specimen. This may obviate the presence of shear stress subjected to the uneven tensioning of the ball bearing 21 and keep two-axis centering balance within the whole system in order to ensure a high standard test accuracy.

Besides, the distance between the grips 50 and 50' is adjustable by operating the hydraulic jacks 60, the test machine 10 of the present invention is capable of testing non-linear specimen and accommodating the size of the specimen which is not necessary in a standard length.

Note that the specification relating to the above embodiment should be construed as exemplary rather than as limitative of the present invention, with many variations and modifications being readily attainable by a person of average skill in the art without departing from the spirit or scope thereof as defined by the appended claims and their legal equivalents.

We claim:

1. A device for testing torsion, tension-compression of a specimen comprising:

A frame including a pair of upright columns secured spaced apart to a foundation, an upper crosshead system slidably engaged on the columns actuated by a pair of hydraulic lifting means disposed to a outmost position of the frame parallel to the columns and fixed by a pair of hydraulic brake members inside said upper crosshead system, a lower crosshead system having a base seat transversely secured on the upright columns and integrated with the pair of hydraulic lifting means, a hollow sphere means secured to a spherical receiving space in a center of the upper crosshead system for movably suspending from a ball head of a ball bearing to which an upper specimen grip is connected and fastened by a load cell, a rotatable hydraulic cylinder and a linear hydraulic cylinder secured spaced apart within a cylindrical outer housing which disposes between a circular cavity in a central underside of the base seat and the foundation and secured by fastening means and an actuator shaft slidably disposed into the rotatable hydraulic cylinder engaged by a linear bearing therebetween having a first and connected to a lower specimen grip and a second threaded end inserted into the linear hydraulic cylinder and secured by a fixture means inside the linear hydraulic cylinder with a first and second rotatable bearing means engaged therebetween;

Whereby said upper specimen grip enables to make self-alignment prior to be secured by at least three hydraulic buckle members and said lower specimen grip enables to rotate alternately and to slide vertically relative to the upper specimen grip.

2. A device as recited in claim 1 wherein said upper crosshead system includes an upper base plate combined with a lower base plate and secured by screw means wherein said upper base plate has a pair of first vertical bore formed spaced apart adjacent two lateral ends thereof engageable with the pair of upright columns, a pair of first conduits and a pair of second conduits respectively connected to a pair of first rectangular cavities in an underside of said upper base plate abutting the vertical bores, a plurality of first vertical screw holes formed spaced apart, a semisphare cavity in a center underside communicated to a third conduit in a center top thereof; said lower base plate is integrated with the pair of lifting means and a pair of second rectangular cavities formed spaced apart in an upper surface engageable with the first rectangular cavities, a hemisphere central bore engageable with the hemisphere cavity and a plurality of second vertical screw holes engageable with the first vertical screw holes.

3. A device as recited in claim 1 wherein said hydraulic lifting means each includes a base integrated with the foundation, and an axial rod of T shaped section having a first end connected to the lateral ends of the lower base plate and a lower end axially inserted into a vertical cylinder so as to define a pair of fifth and sixth hydraulic chambers therebetween, said vertical cylinder projected upward from the base and having a pair of fifth and sixth hydraulic conduits in a peripheral wall respectively communicated with said fifth and sixth chambers and an external hydraulic source, and a central opening for slidably engaging with the axial rod therein.

4. A device as recited in claim 1 wherein said hydraulic brake members are respectively disposed into the rectangular cavities of said upper crosshead system and each includes a rectangular cylinder, a piston, a cover and a sphere faced clamp lock coaxially and slidably secured to the rectangular cylinder by screw means, said rectangular cylinder being defined a pair of third and fourth hydraulic chambers therein and respectively communicated with an external hydraulic source via a third and fourth conduits inside said upper crosshead system.

5. A device as recited in claim 1 wherein said base seat of the lower crosshead system includes a pair of vertical holes formed spaced apart adjacent two lateral ends thereof for fixedly engaging the base seat onto the upright columns and a circular cavity abutting a central bore centrally formed in an underside thereof.

6. A device as recited in claim 1 wherein said hollow sphere means includes an upper hollow semispherical part combined with a lower hollow semispherical part secured integrally into the upper crosshead system, said upper part including a plurality of vertical screw holes, a central bore and at least three hydraulic buckle member slidabley secured spaced apart therewithin and respectively communicated with an external hydraulic source via a plurality of first and second conduits which converge upon a central port in a top of the upper crosshead system, said lower part including a plurality of vertical screw holes engageable with the corresponding vertical screw holes of the upper part, at least three buckle slots formed spaced apart around an upper rim and a tapered central bore for passing through an axial rod of the ball bearing.

7. A device as recited in claim 6 wherein said hydraulic buckle members each includes a piston, an annular ring and a sphere faced clamp lock coaxially and slidably secured by screw means and defining a first and second hydraulic chamber with the upper part of said hollow sphere means.

8. A device as recited in claim 6 further includes a stress sensor attached to each of said hydraulic buckle members for sending the tension information of the buckle member to an external computer and making stress compensations automatically to the buckle members.

9. A device as recited in claim 1 wherein said rotatable hydraulic cylinder includes a tubular casing having a pair of first tapered extension symmetrically extended inward from an inner periphery along the length thereof each including a sealing means on their forward edges, a pair of cover means covering two ends of the casing and secured by screw means and each having a circular central bore for permitting the insertion of said actuator shaft therethrough and a rotatable piston rotatably disposed into the tubular casing having a hollow cylinder body engageable with said first tapered extensions, a central bore of arc lined triangle section and a pair of second tapered extensions symmetrically extended outward from opposite peripheries along the length thereof and engageable with inner periphery of said tubular casing including a sealing means centrally extended along the length of the second tapered extensions so as to define two pairs of vertical hydraulic chambers therein, said chambers respectively communicating with external hydraulic sources via two pairs of conduits positioned spaced apart in the peripheral wall of the tubular casing.

10. A device as recited in claim 1 wherein said linear hydraulic cylinder including a tubular body, a pair of upper and lower cover means covering two ends of the body and secured by screw means through their corresponding screw holes adjacent their circumferences each having a circular central bore in alignment with each other, a linear piston slidably disposed into said tubular body having a cylindrical body longer than said tubular body including a central bore therethrough for engaging with a threaded lower end of said actuator shaft and an annular flange extended outward from a middle periphery including a sealing ring centrally extended along an outer periphery of the flange so as to define a pair of upper and lower hydraulic chambers therebetween, said chamber communicating to an external hydraulic source via a pair of upper and lower conduits formed spaced apart through a peripheral wall of said tubular body.

11. A device as recited in claim 1 wherein said fixture means includes a threaded central bore in an upper end engageable with the threaded lower end of said actuator shaft and a toothed lower end fittable to specific fastening means.

12. A device as recited in claim 1 wherein said linear bearing includes a hollow tubular body of arc lined triangle section engageable with the central bore of said rotatable piston and the actuator shaft which has a large diameter middle portion of arc lined triangle section engageable within said linear bearing.

13. A device as recited in claim 1 further includes a rotation displacement detector (RVDT) attached to a lower end of said rotatable hydraulic cylinder for sending the rotation displacement information of said lower specimen grip to an external computer.

14. A device as recited in claim 1 further includes a linear displacement detector (LVDT) disposed between said rotatable and linear hydraulic cylinders for sending the linear displacement information of said lower specimen grip to the external computer.

* * * * *